United States Patent
Su et al.

(10) Patent No.: US 9,266,804 B2
(45) Date of Patent: *Feb. 23, 2016

(54) DUAL-BED CATALYTIC DISTILLATION TOWER AND METHOD FOR PREPARING DIMETHYL ETHER USING THE SAME

(71) Applicant: CPC Corporation, Taiwan, Taipei (TW)

(72) Inventors: Wei-Bin Su, Chiayi (TW); Karl Tze-Tang Chuang, Chiayi (TW); Tzong-Bin Lin, Chiayi (TW); Cheng-Tsung Hong, Chiayi (TW); Hung-Chung Shen, Chiayi (TW); Yung-Sheng Ho, Chiayi (TW)

(73) Assignee: CPC Corporation, Taipei (TW)

( * ) Notice: Subject to any disclaimer, the term of this patent is extended or adjusted under 35 U.S.C. 154(b) by 197 days.

This patent is subject to a terminal disclaimer.

(21) Appl. No.: 14/040,982

(22) Filed: Sep. 30, 2013

(65) Prior Publication Data

US 2014/0058137 A1    Feb. 27, 2014

Related U.S. Application Data

(63) Continuation-in-part of application No. 12/957,470, filed on Dec. 1, 2010, now Pat. No. 8,575,399.

(51) Int. Cl.
| | | |
|---|---|---|
| *C07C 41/09* | (2006.01) | |
| *B01J 8/04* | (2006.01) | |
| *B01D 3/00* | (2006.01) | |

(Continued)

(52) U.S. Cl.
CPC ............. *C07C 41/09* (2013.01); *B01D 3/009* (2013.01); *B01J 8/0453* (2013.01); *B01J 27/053* (2013.01); *B01J 27/12* (2013.01); *B01J 29/40* (2013.01); *B01J 29/7007* (2013.01); *B01J 31/08* (2013.01); *B01J 35/0006* (2013.01); *B01J 2208/00265* (2013.01); *B01J 2208/00274* (2013.01); *B01J 2208/00283* (2013.01); *B01J 2208/00539* (2013.01); *B01J 2208/025* (2013.01); *B01J 2219/00006* (2013.01)

(58) Field of Classification Search
None
See application file for complete search history.

(56) References Cited

U.S. PATENT DOCUMENTS

| | | | |
|---|---|---|---|
| 3,036,134 A | 5/1962 | Mattox et al. | |
| 5,490,941 A | 2/1996 | Miyabe et al. | |
| 5,684,213 A | 11/1997 | Nemphos et al. | |
| 5,750,799 A | 5/1998 | van Dijk | |
| 5,908,963 A | 6/1999 | Voss et al. | |

(Continued)

FOREIGN PATENT DOCUMENTS

WO    WO2007014534    2/2007

OTHER PUBLICATIONS

Siril, et al. "New polystyrene sulfonic acid resin catalysts with enhanced acidic and catalytic properties"; Journal of Molecular Catalysis, A: Chemical 279, 63-68, 2008.

*Primary Examiner* — Rosalynd Keys
(74) *Attorney, Agent, or Firm* — Fishman & Associates, LLC.

(57) ABSTRACT

A dual-bed catalytic distillation tower has a catalytic column having an upper catalytic bed filled with low temperature dehydration catalysts and a lower catalytic bed filled with high temperature dehydration catalysts. When using the dual-bed catalytic distillation tower, the feeding may be fed to the tower at the top of the upper catalytic bed, between the upper and lower catalytic beds, or at the bottom of the lower catalytic bed for dehydration to obtain DME. The dual-bed catalytic distillation tower has the advantage of flexible set-up depending on various feedings such as anhydrous or crude methanol and on different grades of DME to be obtained.

14 Claims, 7 Drawing Sheets

(51) Int. Cl.
*B01J 35/00* (2006.01)
*B01J 27/053* (2006.01)
*B01J 27/12* (2006.01)
*B01J 29/40* (2006.01)
*B01J 29/70* (2006.01)
*B01J 31/08* (2006.01)

(56) References Cited

U.S. PATENT DOCUMENTS

| | | |
|---|---|---|
| 6,045,762 A | 4/2000 | Chuang et al. |
| 6,740,783 B1 | 5/2004 | Jun et al. |
| 2007/0066855 A1 | 3/2007 | Malandrino et al. |
| 2007/0095646 A1 | 5/2007 | Wu et al. |
| 2010/0292071 A1 | 11/2010 | Ferrini et al. |

(a) One-step process:

(b) Two-step process:

DUAL-BED CATALYTIC DISTILLATION TOWER AND METHOD FOR PREPARING DIMETHYL ETHER USING THE SAME

CROSS-REFERENCE TO RELATED APPLICATION

This application is a continuation-in-part of U.S. application Ser. No. 12/957,470 filed on Dec. 1, 2010, which is incorporated by reference in the present application in its entirety.

BACKGROUND OF THE INVENTION

1. Field of the Invention

The present invention relates to a catalytic distillation tower used for preparing dimethyl ether (DME), especially a dual-bed catalytic distillation tower. The present invention also relates to a method for preparing dimethyl ether using the same.

2. Description of the Prior Arts

Dimethyl ether (DME) is prepared by using different raw materials such as coal, nature gas, petroleum coke and bio-char. The methanol is firstly prepared from the raw materials, and the methanol is dehydrated to obtain DME. In the dehydration reaction, catalysts are needed to carry out the reaction. Solid-state acid catalysts such as zeolite, silicone, aluminum oxide, resin etc. (Spivey, J. J., 1991) or modified acid ion exchange resin (U.S. Pat. No. 6,740,783) are commonly used in the dehydration. Resin catalysts are low temperature catalysts with reaction temperatures ranging from 70 to 150° C. and almost 100% conversion of methanol can be obtained. However, the low temperature catalysts cannot bear high temperature. Other catalysts are high temperature catalysts with reaction temperatures ranging from 200 to 350° C. When the reaction temperature is getting higher, however, methanol and DME will be further dehydrated to C2-C4 olefin, thereby resulting in the loss of catalyst activity and reduction of DME yield.

Further, to reduce the energy consumption during the catalytic distillation process, the catalysts are put in the catalytic distillation tower so the heat generated from the methanol dehydration reaction can be used for catalytic distillation. The requirement for this catalytic distillation process is that the catalytic reaction and distillation can happen at the similar tower pressure and temperature range.

US 2007/0066855 A1 discloses a method for production of DME using catalytic distillation tower so the heat generated from dehydration can be fully used and reduce the production cost. However, the tower temperature and pressure used for dehydration reaction result in that methanol and water in the stripping column cannot be separated easily. FIG. 1 shows the relative volatility of methanol and water at different tower pressures and can be used to calculate and estimate the difficulty for separating methanol and water at high tower pressure. FIG. 1 shows that the relative volatility of methanol and water reaches 1 (i.e. the azeotropic zone) when the mole fraction of liquid water equals 0.825 at a tower pressure of 18 bar. Azeotrope composition of methanol and water results in separation difficulties.

WO 2007/014534 provides high temperature dehydration in the catalytic distillation tower by using high temperature dehydration catalysts at a reaction temperature ranging from 160 to 180° C. and under a tower pressure ranging from 18 to 23 bar. However, the energy consumption of the condenser and reboiler increases in order to drive the catalytic reaction under high temperatures. U.S. Pat. No. 5,684,213 mentions high temperature dehydration reaction at a reaction temperature ranging from 350 to 400° C. and under 600 psi of tower pressure. When dehydration is carried out at such a high temperature, olefin side products increase to cause the decay of catalyst activity, resulting in lower DME yield. Hydrogen is added to the catalytic distillation tower to inhibit undesired side products generated. However, adding hydrogen increases the production cost and the reaction complexity.

The technique of using low temperature dehydration catalysts in the catalytic distillation tower is also disclosed. For example, WO 2007/014534 provides that dehydration reaction is carried out at a reaction temperature ranging from 130 to 158° C. and under a tower pressure ranging from 10 to 18 bar by using low temperature acid ion exchange catalysts. However, the low temperature catalysts can only be used at temperature lower than 140° C. When the reaction is carried out at a low temperature and pressure, the dew point of high purity DME at the top of the tower will decrease. For example, the dew point of DME becomes 40.3° C. when the tower pressure is as low as 9 bar and therefore using 20° C. industrial water to condense DME will be impractical. When the tower pressure is adjusted to 12 bar, the temperature at the catalytic column will be higher than 150° C., and the low temperature catalysts will be damaged.

All the above-mentioned methods use single-bed catalytic system in the catalytic distillation tower, i.e. only high temperature or low temperature dehydration reaction is carried out. In the conventional methods, the catalytic distillation tower cannot be easily adjusted depending on the grades of the feeding methanol and of the obtained DME because none of the conventional methods can provide suitable and complementary tower temperature and pressure conditions.

SUMMARY OF THE INVENTION

Therefore, the purpose of the present invention is to provide a catalytic distillation method for preparing dimethyl ether (DME) in which the tower temperature and pressure can be properly adjusted depending on the relation among DME, methanol and water in the catalytic distillation and the dehydration catalysts selected.

Specifically, the present invention relates to a dual-bed catalytic distillation tower and a method for preparing DME using the same.

The present invention provides a dual-bed catalytic distillation tower comprising a catalytic column. The catalytic column comprises an upper catalytic bed and a lower catalytic bed. The upper catalytic bed is filled with low temperature dehydration catalysts and the lower catalytic bed is filled with high temperature dehydration catalysts. At least one feed port is located at the top of the upper catalytic bed, between the upper catalytic bed and the lower catalytic bed, and at the bottom of the lower catalytic bed.

Preferably, the low temperature dehydration catalyst is a non-halogenated divinyl-benzene cross-linked sulfonated polystyrene resin.

Preferably, the non-halogenated divinyl-benzene cross-linked sulfonated polystyrene resin has an acid capacity more than 4 meq/g and a specific surface area more than 20 m$^2$/g. More preferably, the non-halogenated divinyl-benzene cross-linked sulfonated polystyrene resin has an acid capacity ranging from 4 meq/g to 6 meq/g and a specific surface area ranging from 20 m$^2$/g to 70 m$^2$/g.

More specifically, the non-halogenated divinyl-benzene cross-linked sulfonated polystyrene resin comprises Amberlyst® 15 acid ion exchange resin, Amberlyst® 35 acid ion exchange resin, Purolite® CT-275, Purolite® CT-276 or any combination thereof.

Preferably, the high temperature dehydration catalyst is halogenated divinyl-benzene cross-linked sulfonated polystyrene resin. For example, but not limited to, the halogenated divinyl-benzene cross-linked sulfonated polystyrene resin is chlorinated divinyl-benzene cross-linked sulfonated polystyrene resin.

Preferably, the halogenated divinyl-benzene cross-linked sulfonated polystyrene resin has an acid capacity more than 2 meq/g and a specific surface area more than 20 $m^2/g$. More preferably, the halogenated divinyl-benzene cross-linked sulfonated polystyrene resin has an acid capacity ranging from 2 meq/g to 6 meq/g and a specific surface area ranging from 20 $m^2/g$ to 60 $m^2/g$.

More specifically, the halogenated divinyl-benzene cross-linked sulfonated polystyrene resin comprises Amberlyst® 70 acid ion exchange resin, Purolite® CT-482 or their combination.

The present invention also provides a method for preparing dimethyl ether by using aforesaid dual-bed catalytic distillation tower wherein the catalytic column is used for dehydration of methanol. The feeding stream containing methanol is fed from the feed port located at the top of the upper catalytic bed, between the upper catalytic bed and the lower catalytic bed, or at the bottom of the lower catalytic bed at the tower pressure ranging from 7 to 12 bar for dehydration to obtain DME.

The temperature of the catalytic distillation tower of the present invention is at the range from 40 to 250° C. When the tower temperature is at the range from 85 to 125° C., the low temperature dehydration catalysts are used for dehydration. When the tower temperature is at the range from 125 to 180° C., the high temperature dehydration catalysts are used for dehydration.

Preferably, the catalytic distillation tower further comprises at least one flash zone at the top of the upper catalytic bed, between the upper catalytic bed and the lower catalytic bed, and at the bottom of the lower catalytic bed; the at least one flash zone is reserved for heat exchange and reflux.

When anhydrous methanol is used as the feeding, the anhydrous methanol is fed to the tower from the feed port located at the top of the upper catalytic bed.

When syngas is used as the feeding, the syngas is firstly converted to a mixture containing DME, methanol and water, and the mixture is fed to the tower from the feed port located at the top of the upper catalytic bed or between the upper and the lower catalytic beds.

When crude methanol is used as the feeding, the crude methanol is fed to the tower from the feed port located at the bottom of the lower catalytic bed or between the upper and the lower catalytic beds.

Compared to the conventional single-bed catalytic distillation tower, the dual-bed catalytic distillation tower of the present invention has advantages of flexible set-up depending on various types of feedings such as anhydrous or crude methanol and on different grades of DME to be obtained.

DETAILED DESCRIPTION OF THE INVENTION

The above and other technical features and advantages of the present invention will be described in greater detail with reference to the drawings.

Figure 1:
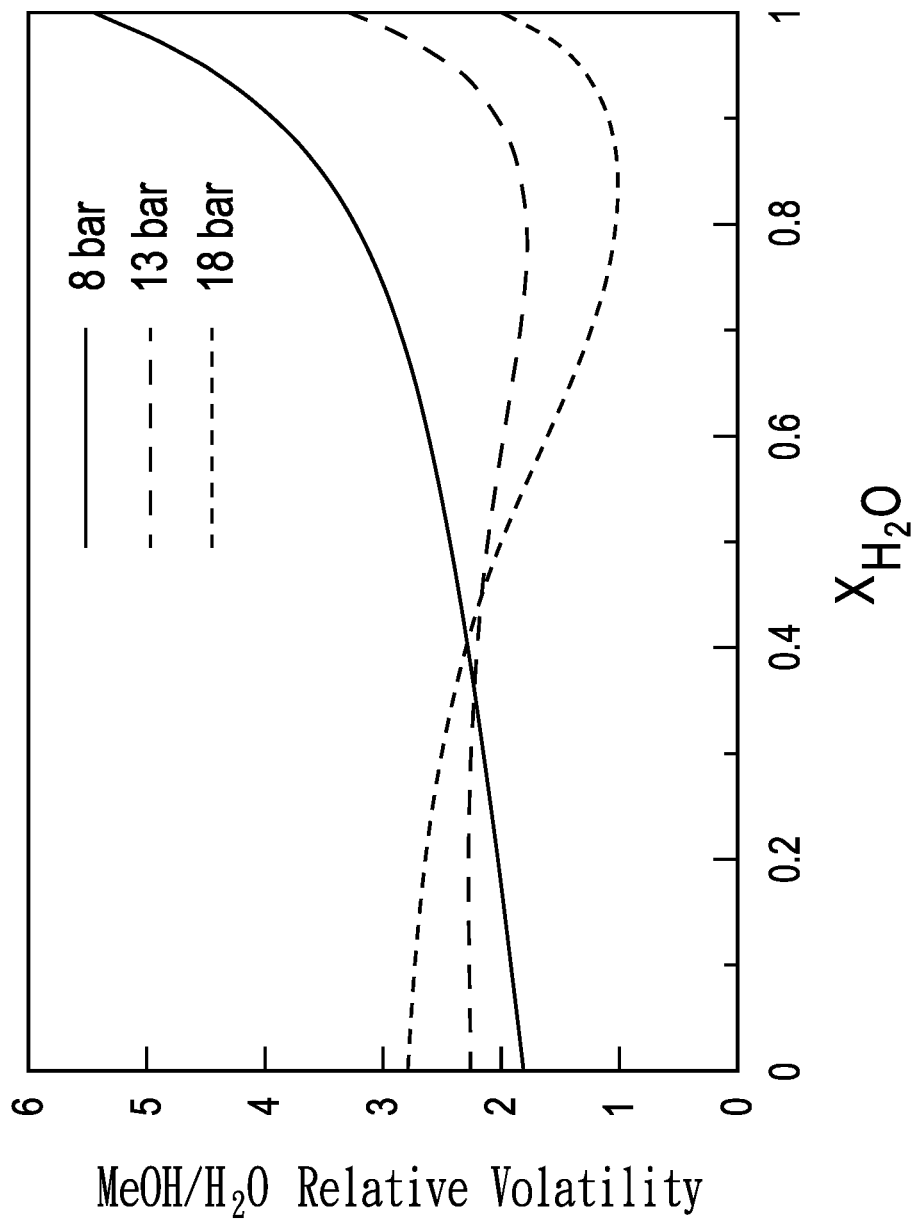
FIG. 1 is a diagram showing the changes of relative volatility of methanol and water at different tower pressures.
Figure 2:
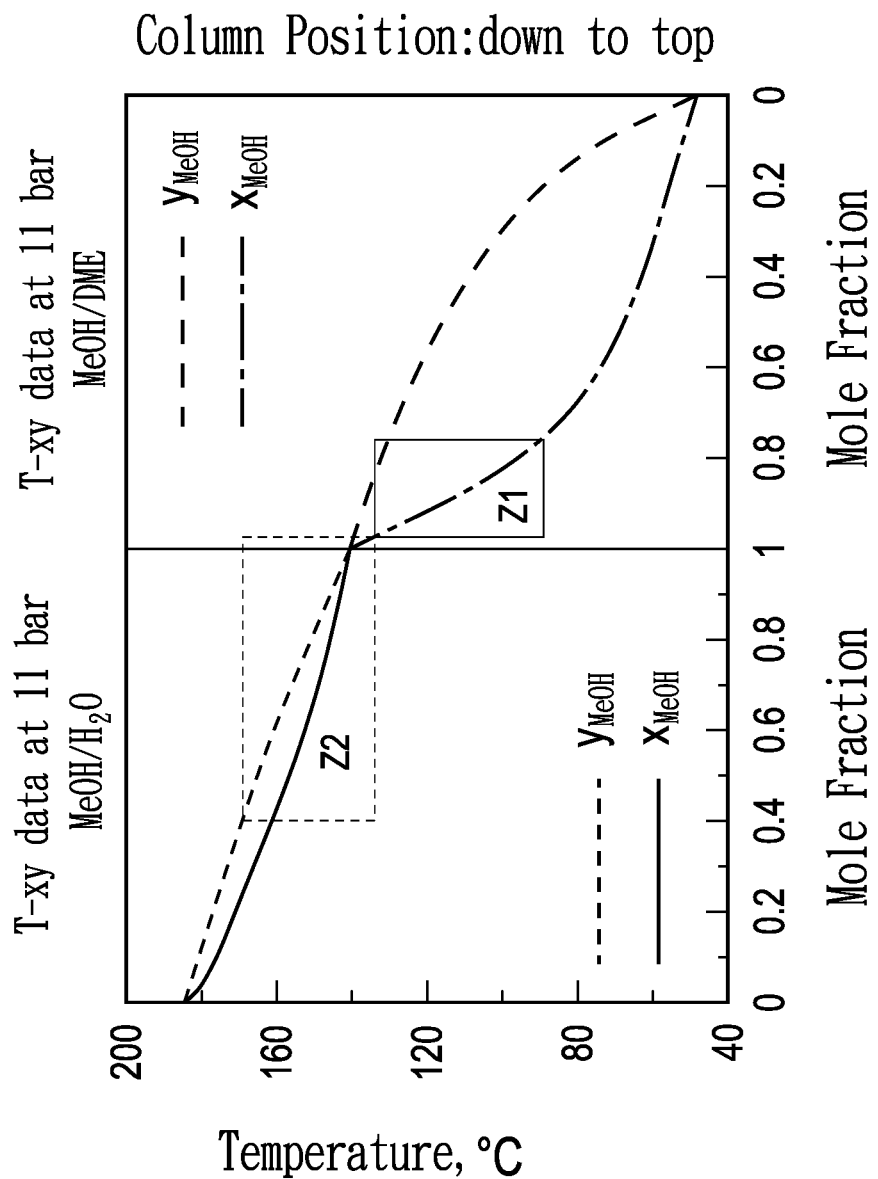
FIG. 2 is a liquid-gas phase diagram showing the equilibrium relation between methanol and DME as well as methanol and water at different temperatures under 11 bar.

FIG. 2 is a liquid-gas phase diagram showing the equilibrium relation between two substances at different temperatures under 11 bar. The right part of FIG. 2 shows the equilibrium relation between methanol and dimethyl ether (DME). As shown in FIG. 2, when the temperature is close to the saturated liquid temperature of methanol, i.e. 140.5° C., the concentration of methanol increases from the top to bottom of the catalytic distillation tower and the concentration of liquid phase methanol is higher than the concentration of gas phase methanol at the same position of the tower. Therefore, the low temperature dehydration catalyst can be used for dehydration when the dehydration is performed under the conditions shown in Z1 zone in FIG. 2. The left part of FIG. 2 shows the equilibrium relation between methanol and water. When the temperature is close to the saturated liquid temperature of methanol, the concentration of methanol increases from bottom to top of the catalytic distillation tower and the concentration of gas phase methanol is higher than the concentration of liquid phase methanol at the same position of the tower. Therefore, the high temperature dehydration catalyst can be used for dehydration when the dehydration is performed under the conditions shown in Z2 zone in FIG. 2. The saturated liquid temperature of methanol varies with tower pressure. When the tower pressure is lower than 11 bar, the saturated liquid temperature of methanol becomes lower than 140.5° C. On the contrary, the saturated liquid temperature of methanol becomes higher than 140.5° C. when the tower pressure is higher than 11 bar.

Figure 3:
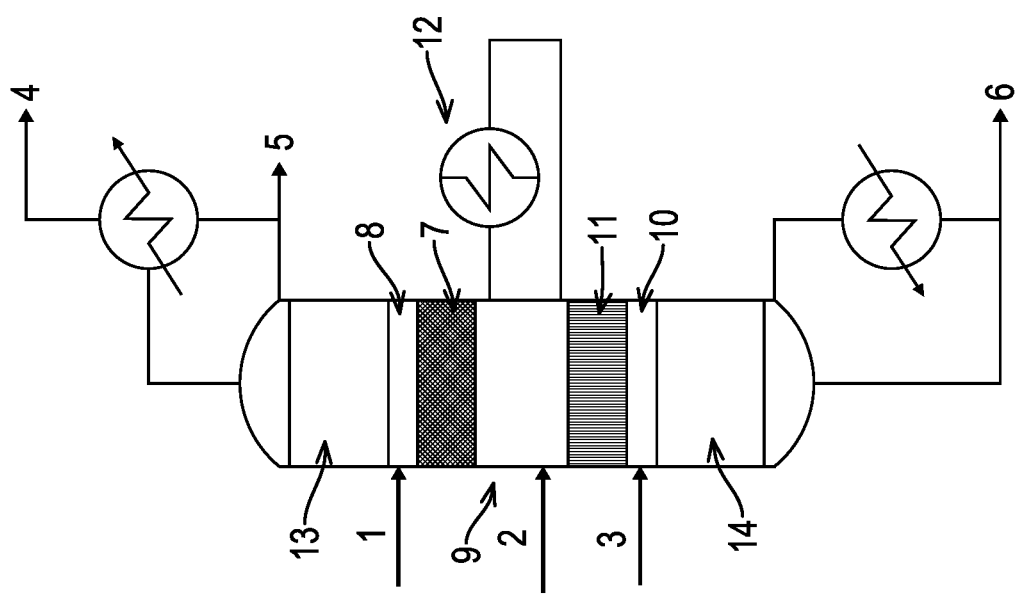
FIG. 3 is a schematic diagram showing the dual-bed catalytic distillation of the present invention.

Based on the substance properties as described above, the present invention provides a catalytic distillation tower where different catalysts can be placed in different temperature zones to carry out dehydration of methanol efficiently and prevent the catalysts from being damaged due to high temperature. As shown in FIG. 3, the catalytic column in the catalytic distillation tower of the present invention comprises an upper catalytic bed 7 and a lower catalytic bed 11. Three flash zones 8, 9, 10 are respectively located at the top of the upper catalytic bed 7, between the upper catalytic bed 7 and the lower catalytic bed 11, and at the bottom of the lower catalytic bed 11. Three feed ports 1, 2, 3 are respectively located at the flash zones 8, 9, 10. A heat exchanger and/or reflux condenser 12 is located between the upper catalytic bed 7 and the lower catalytic bed 11.

Generally, the temperature of the catalytic distillation tower of the present invention is from 40° C. to 250° C. When the tower temperature is from 85° C. to 125° C., the low temperature dehydration catalyst is used in Z1 as shown in FIG. 2, i.e. the high liquid phase methanol concentration zone. When the tower temperature is from 125° C. to 180° C., the high temperature dehydration catalyst is used in Z2 as shown in FIG. 2.

Preferably, the low temperature dehydration catalyst is used in the upper catalytic bed 7. For example, but not limited to, Amberlyst® 15 acid ion exchange resin is used at tower temperatures ranging from 85 to 110° C., Amberlyst® 35 acid ion exchange resin is used at tower temperatures ranging from 85 to 125° C., Purolite® CT-275 acid ion exchange resin is used at tower temperatures ranging from 85 to 125° C., and Purolite® CT-276 acid ion exchange resin is used at tower temperatures ranging from 85 to 125° C. The high temperature dehydration catalyst is used in the lower catalytic bed 11. For example, but not limited to, Amberlyst® 70 acid ion exchange resin is used at tower temperatures ranging from 125 to 180° C. and Purolite® CT-482 acid ion exchange resin is used at tower temperatures ranging from 125 to 180° C.

The tower pressure varies depending on the environment. The pressure is usually in the range from 6 bar to 30 bar, preferably from 7 bar to 12 bar. When the catalytic distillation tower is used at high latitudes, 20° C. industrial water is available to condense the DME with a dew point of 25.4° C., the tower pressure can be as low as 6 bar. When the tower pressure is operated at 18 bar, the relative volatility of methanol and water should be considered.

The feeding can be fed into the catalytic distillation tower from different feed ports 1, 2 and 3. When anhydrous methanol is used as the feeding, the anhydrous methanol is usually dehydrated in liquid phase so it is fed to the tower from feed port 1 located at the top of the upper catalytic bed 7. When syngas is used as the feeding, the syngas is firstly converted to a mixture containing dimethyl either, methanol and water, and the mixture is usually fed to the tower from feed port 1 located at the top of the upper catalytic bed 7 or feed port 2 located between the upper catalytic bed 7 and the lower catalytic bed 11. When crude methanol is used as the feeding, the crude methanol is firstly heated to saturated vapor for further reaction so it is usually fed to the tower from feed port 3 located at the bottom of the lower catalytic bed 11 or feed port 2 between the upper catalytic bed 7 and the lower catalytic bed 11. The heat exchanger and/or reflux condenser 12 located between the upper catalytic bed 7 and the lower catalytic bed 11 is used to control the temperatures of the two catalytic beds and simultaneously protect the low temperature dehydration catalysts in the upper catalytic bed 7 from being damaged due to high temperature.

As shown in FIG. 3, the catalytic distillation tower further contains a rectification column 13 at the top of the catalytic column and a stripper column 14 under the catalytic column. After reaction in the catalytic distillation tower, the mixture of DME and carbon dioxide is discharged from a condenser outlet 4 and DME is discharged and collected from a condenser outlet 5. Unreacted feeding stream flows into the reboiler on the bottom of the tower for vaporization and water goes out from a reboiler outlet 6.

Figure 4:
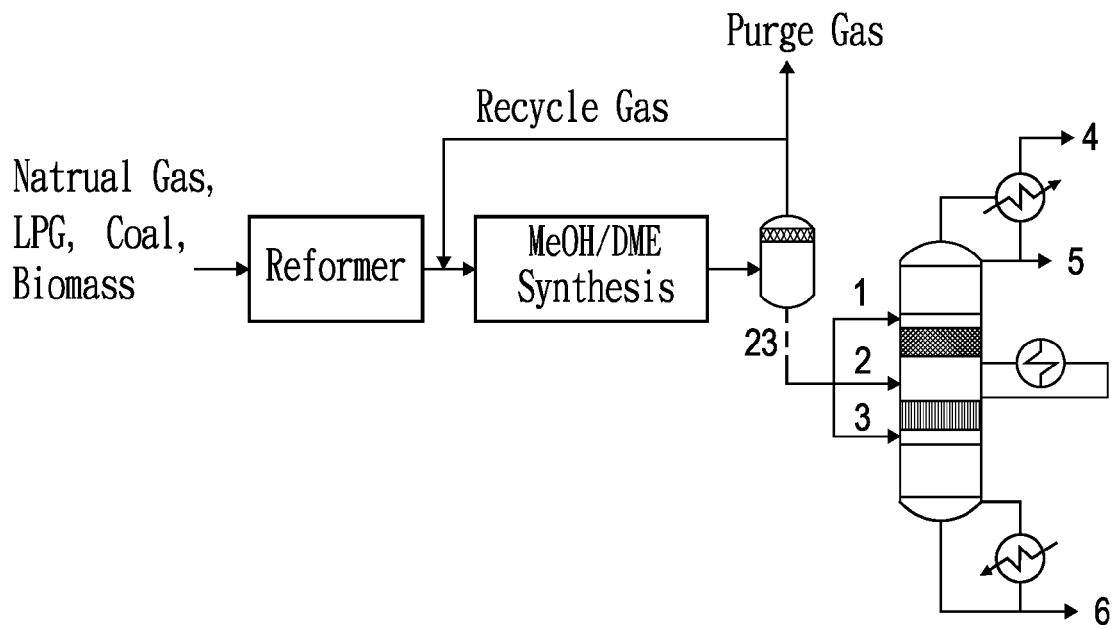
FIG. 4 is a schematic diagram showing DME preparation methods using the dual-bed catalytic distillation tower of the present invention.
Figure 4:
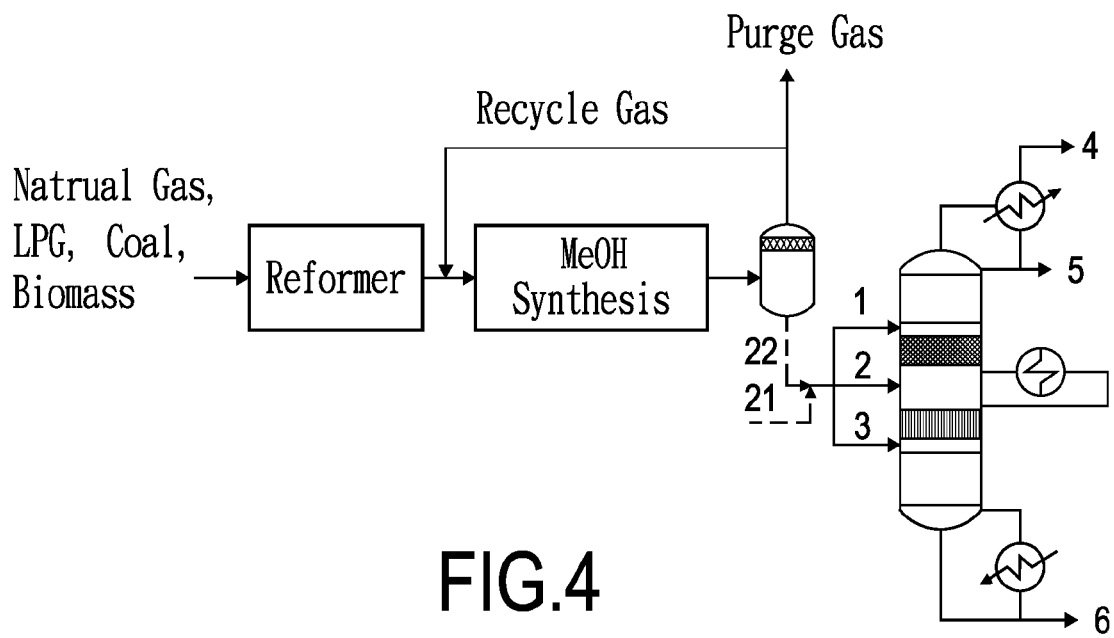

FIG. 4 shows the application of the dual-bed catalytic distillation tower in the preparation of DME. FIG. 4(a) shows how the dual-bed catalytic distillation tower works in one-step preparation of DME. After the one-step reaction, mixture stream 23 containing DME, methanol, water and carbon dioxide may be fed into the dual-bed catalytic distillation tower from different feed ports 1, 2 and 3 for dehydration to obtain DME. FIG. 4(b) shows how the dual-bed catalytic distillation tower works in two-step preparation of DME. For the two-step process, the crude methanol stream 22 and anhydrous methanol stream 21 may be fed into the dual-bed catalytic distillation tower from different feed ports 1, 2 and 3 for dehydration to obtain DME.

EXAMPLES

In the following examples, low temperature dehydration rate (An et al., 2004), thermodynamic NRTL-RK equation, the thermodynamic data for high temperature dehydration reaction (Lin et al., 1981; Hayashi, 1982) were used for theoretical calculation of the DME catalytic distillation tower by the simulation software "Aspen Plus" to illustrate the feasibility of the present invention.

The catalytic distillation tower from the top down contained an overhead condenser, a rectification column, a catalytic column, a stripping column and a reboiler at the tower bottom.

The conditions for the conventional single-bed catalytic distillation tower were set as follows. The theoretical plate numbers of the rectification column and the stripping column were respectively set to 7 (including part of or all of the condenser and reboiler). The feed containing methanol mixture was fed to the catalytic distillation tower at 30° C., and performed heat exchange with the hot water leaving the bottom of the catalytic distillation tower. The feed temperature was about 40° C. after the heat exchange step. The amount of catalyst and the tower height were adjusted, i.e. changing the plate number of the catalytic column and the tolerated flow rate for liquid in the catalytic column (24 inch height/plate) to be 24.4 m/s. Afterwards, the reflux ratio and D/F were adjusted so the concentration of DME and water produced from the catalytic distillation tower were respectively 99.9 wt %.

In the dual-bed catalytic distillation tower, the catalytic column included an upper catalytic bed filled with low temperature dehydration catalysts and a lower catalytic bed filled with high temperature dehydration catalysts. The position in the tower having a temperature of 135° C. was set as the demarcation point for the upper and lower catalytic beds. The plate number of the catalytic column, the reflux ratio and D/F were adjusted so the concentration of DME and water produced from the catalytic distillation tower were respectively 99.9 wt %. When the fuel grade DME (93 wt % of DME and 7 wt % of methanol) was desired under the same catalytic distillation design, the amount of catalysts was excessive. In this situation, the feeding was increased to lower the conversion of methanol, such that the fuel grade DME was obtained from the top of the tower, and the concentration of the water obtained from the bottom of the catalytic distillation tower was still 99.9 wt %.

The conditions of the present dual-bed catalytic distillation tower were assumed as below. The unit volume of the upper catalytic bed equaled 0.6 unit volume of the theoretical plate and the unit volume of the lower catalytic bed equaled 0.85 unit volume of the theoretical plate (referring to U.S. Pat. No. 6,045,762 and US 2007/0,095,646). The dehydration rate of the hydrophobic and strong acidic catalysts was five times more than the rate disclosed in the literature of Lin et al., 1981.

Comparative Example

Anhydrous Methanol as Feeding (Prior Art)

The simulation for the production of DME in US 2007/0,066,855 was indicated below.

| | |
|---|---|
| Tower pressure | 12 bar |
| Pressure drop | 0.7 bar |
| Reflux ratio | 2 |
| D/F weight ratio | 0.71773 |
| Theoretical plates | 30 |
| Feeding plate | At plate number 8 |
| Catalyst column | From plates number 10 to 18 |
| Catalyst amount | 140 m$^3$ |
| Methanol fed | 5013 tpd (99.88 weight %) |
| DME produced | 3596 tpd (92.35 weight %) |
| Temperature on the top of the tower | 56.1° C. |
| Temperature on the bottom of the tower | 18.9° C. |

The result showed that the DME production rate is 3598 tpd (99.61 weight %) and the temperatures at the top and bottom of the tower were respectively 52° C. and 190° C. Although the tower temperature distribution was not disclosed in the prior art, the temperature was assumed having 4° C. inaccuracy compared to the simulated tower temperature.

The result showed that the temperatures at the bottom two plates, i.e. plates 17 and 18, were respectively 151.5° C. and 156.4° C., which exceed the limit of temperature resistance of acid ion exchange resin catalysts such as Amberlyst® 35 having temperature resistance at 140° C. Therefore, the low temperature dehydration catalysts could not be used in the conventional catalytic distillation tower under certain tower pressure such as at the pressure ranging from 8 to 12 bar.

Example 1

Anhydrous Methanol as Feeding

The simulation for the production of DME in the dual-bed catalytic distillation tower of the present invention and in the conventional single-bed catalytic distillation tower was indicated below.

| | |
|---|---|
| Tower pressure | 11 bar |
| Pressure drop | 0.025 bar |
| Initial reflux ratio | 4 |
| D/F molar ratio | 0.4997 |
| Feeding plate | At plate number 7 |

Figure 5:
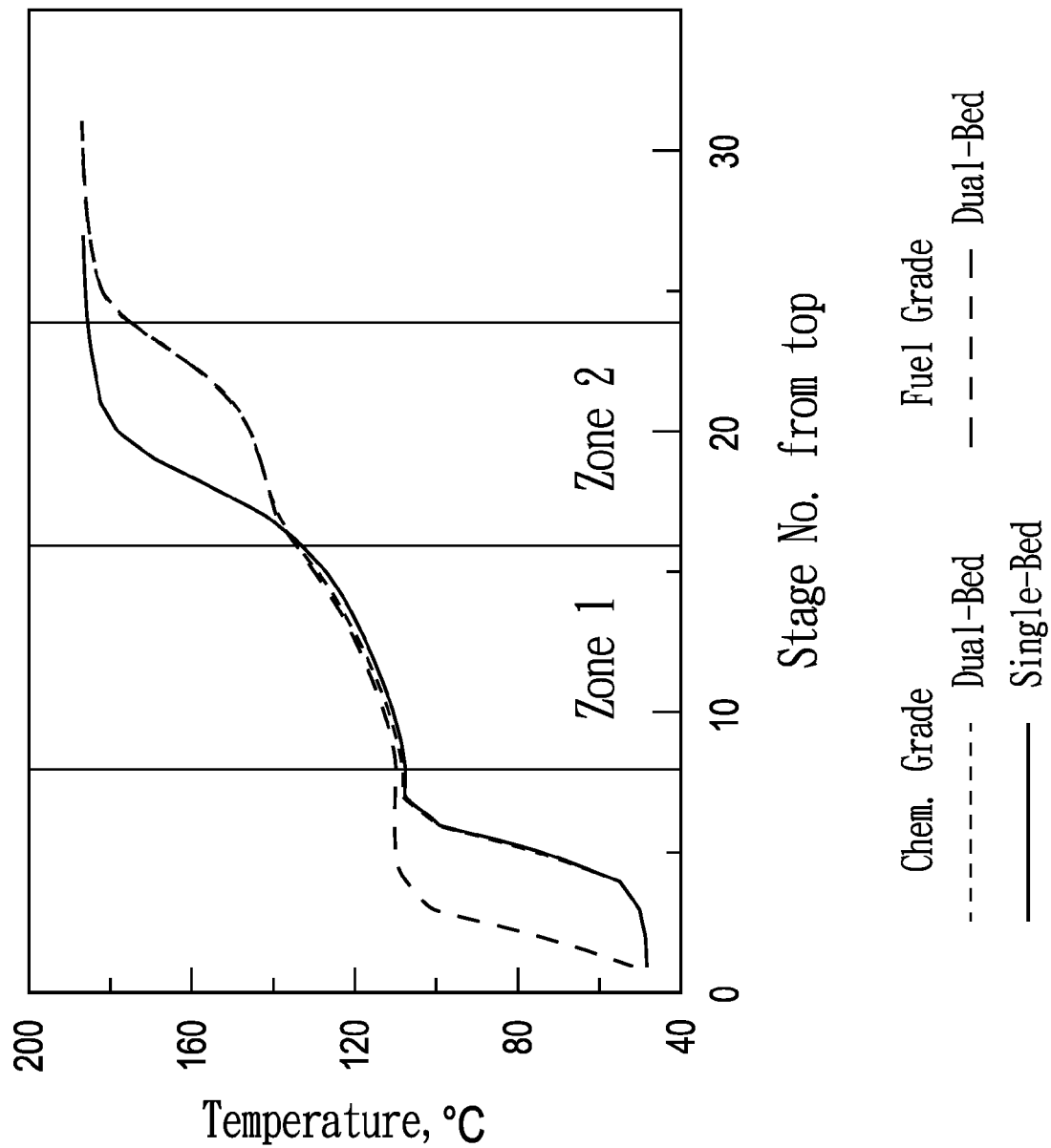
FIG. 5 is a diagram showing the tower temperature distribution in the catalytic distillation tower of the present invention with anhydrous methanol feeding.

The results were shown in Table 1, Table 2 and FIG. 5.

TABLE 1

Stream composition during the catalytic distillation process

| | Catalytic Column | | | | | | | | |
|---|---|---|---|---|---|---|---|---|---|
| DME grade | Single-bed* Chemical | | | Dual-bed Chemical | | | Dual-bed Fuel | | |
| Stream*** | 1 | 5 | 6 | 1 | 5 | 6 | 2 | 5 | 6 |
| Water, kg/hr | 6 | 0 | 1689 | 6 | 0 | 1689 | 7 | 0.1 | 1791 |
| Methanol, kg/hr | 5994 | 4.3 | 1.7 | 5994 | 4.3 | 1.7 | 6693 | 343 | 1.8 |
| DME, kg/hr | 0 | 4305 | 0 | 0 | 4305 | 0 | 0 | 4564 | 0 |
| Total, kg/hr | 6000 | 4309 | 1691 | 6000 | 4309 | 1691 | 6700 | 4907 | 1793 |

*Conventional method, the low temperature dehydration catalyst did not work at high temperature.
***Stream composition at the feed ports 1 and 2, condenser output 5 and reboiler output 6 shown in FIG. 3.

TABLE 2

The results for the preparation of DME using single-bed and dual-bed catalytic distillation towers

| | Catalytic Column | | |
|---|---|---|---|
| | Single-bed* | Dual-bed DME grade | Dual-bed |
| | Chemical | Chemical | Fuel |
| D/F, mole | 0.4993 | 0.4993 | 0.5246 |
| Reflux ratio | 1.728 | 1.768 | 1.106 |
| Feeding plate number | 7 | 7 | 7 |
| Plate number | | | |
| Condenser | 1 | 1 | 1 |
| Rectification column | 2-7 | 2-7 | 2-7 |
| Upper catalytic bed | 8-20 | 8-16 | 8-16 |
| Lower catalytic bed | N/A | 17-24 | 17-24 |
| Stripping column | 21-26 | 25-30 | 25-30 |
| Reboiler | 27 | 31 | 31 |
| Low temperature catalyst, m$^3$ | 19.7 | 13.7 | 13.7 |
| High temperature catalyst, m$^3$ | N/A | 17.2 | 17.2 |
| Tower temperature, ° C. | | | |
| Rectification column | 48.3-108 | 48.3-108 | 52-110 |
| Upper catalytic bed | 108-178 | 108-134 | 110-135 |
| Lower catalytic bed | N/A | 139-177 | 139-177 |
| Stripping column | 182-187 | 183-187 | 183-187 |
| Pressure at tower top, bar | 11 | 11 | 11 |

*Conventional method, the low temperature dehydration catalyst did not work at high temperature.

As shown in Tables 2 and 4, more plates were needed in the dual-bed catalytic distillation tower compared to the single-bed catalytic distillation tower in order to increase methanol conversion rate. This was because the reaction rate of the high temperature dehydration catalyst was lower than the reaction rate of the low temperature dehydration catalyst, so the amount of high temperature dehydration catalyst was more than the amount of low temperature dehydration catalyst. In the present invention, high temperature dehydration catalysts (from plates 17 to 24) were used to replace part of the low temperature dehydration catalysts (from plates 17 to 20) in the conventional catalytic distillation tower, so the temperature increased moderately at the lower catalytic bed. Therefore, the temperature at the border between the upper catalytic bed and the lower catalytic bed would not be too high and damage the low temperature dehydration catalysts in the upper catalytic bed.

Example 2

Crude Methanol as the Feeding

The feeding came from the process for preparing methanol from syngas (with reference to U.S. Pat. No. 5,750,799). The produced methanol containing 10-20 mole % of water was fed to the catalytic distillation tower of the present invention directly for dehydration without further purification. The simulation for the production of DME in the dual-bed catalytic distillation tower of the present invention and in the conventional single-bed distillation tower was indicated below.

| | |
|---|---|
| Tower pressure | 11 bar |
| Pressure drop | 0.025 bar |
| Initial reflux ratio | 4 |
| D/F molar ratio | 0.4997 |

Figure 6:
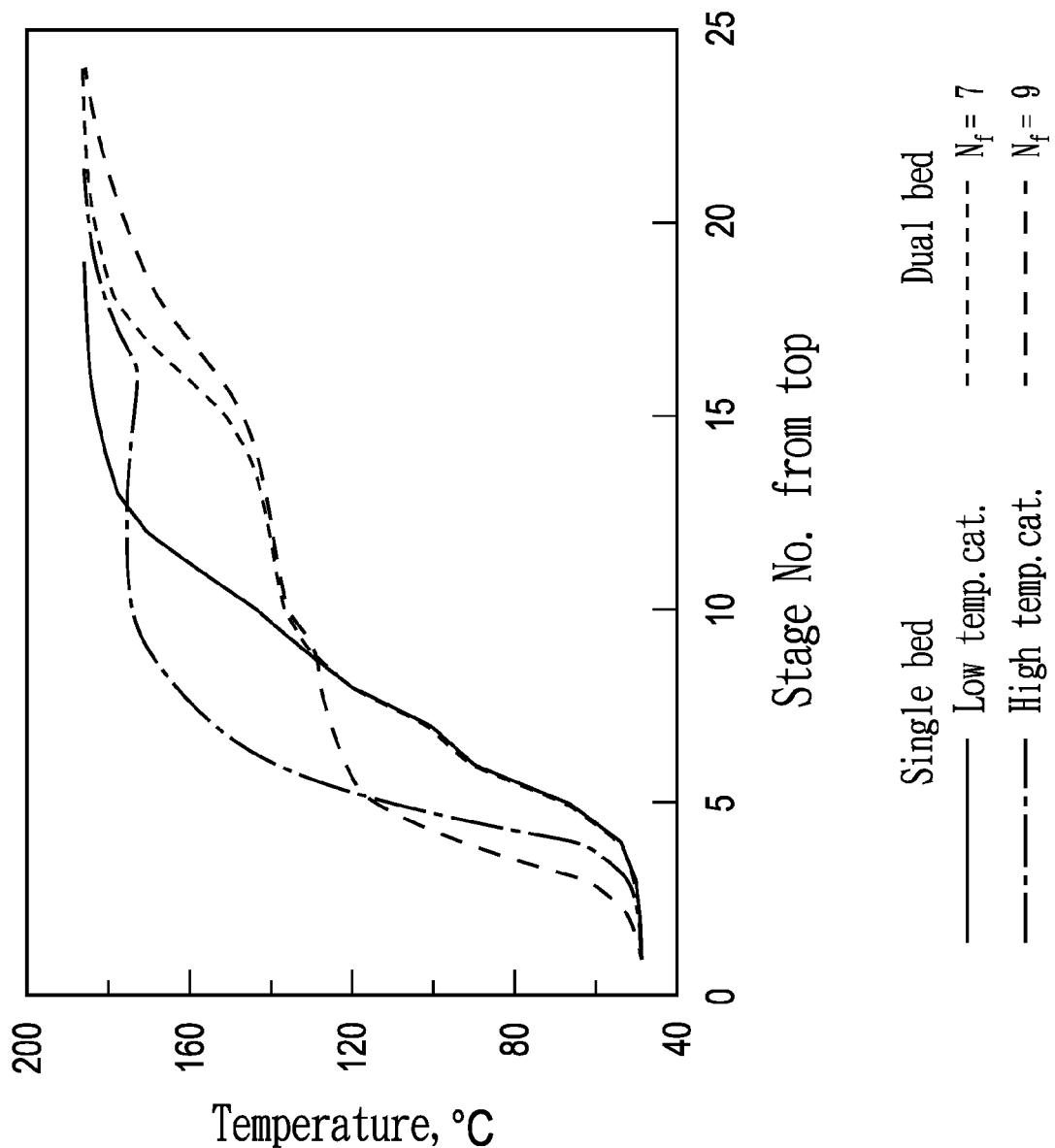
FIG. 6 is a diagram showing the tower temperature distribution in the catalytic distillation tower of the present invention with crude methanol feeding.

The results of using the dual-bed catalytic distillation tower of the present invention and using the conventional single-bed catalytic distillation tower were shown in Table 3, Table 4 and FIG. 6.

TABLE 3

Stream composition during the catalytic distillation process

| | Catalytic Column | | | | | | | | |
|---|---|---|---|---|---|---|---|---|---|
| | Single-bed* | | Dual-bed | | Dual-bed | | Single-bed** | | |
| DME grade | Chemical | | Chemical | | Chemical | | Chemical | | |
| Feeding plate number**** | 7 | | 7 | | 9 | | 16 | | |
| Stream*** | feeding | 5 | 6 | 5 | 6 | 5 | 6 | 5 | 6 |
| water, kg/hr | 666 | 0 | 2349 | 0 | 2349 | 0.08 | 2336 | 0 | 2349 |
| methanol, kg/hr | 5994 | 4.3 | 2.4 | 4.3 | 2.4 | 28.3 | 26.6 | 4.3 | 2.4 |
| DME, kg/hr | 0 | 4304 | 0 | 4304 | 0 | 4270 | 0 | 4304 | 0 |
| Total, kg/hr | 6660 | 4309 | 2351 | 4309 | 2351 | 4298 | 2362 | 4309 | 2351 |

*Conventional method, the low temperature dehydration catalyst did not work at high temperature.
**Conventional method of using high temperature catalysts.
***Stream composition at condenser output 5 and reboiler output 6 shown in FIG. 3.
****Feeding at plate number 7 meant feeding from feed port 1, feeding at plate number 9 meant feeding from feed port 2, feeding at plate number 16 meant feeding from feed port 3.

TABLE 4

The results for the preparation of DME using single-bed and dual-bed catalytic distillation tower with crude methanol

| | Catalytic Column | | | |
|---|---|---|---|---|
| | Single-bed* | Dual-bed | Dual-bed | Single-bed** |
| | | DME grade | | |
| | Chemical | Chemical | Chemical | Chemical |
| Feeding plate number | 7 | 7 | 9 | 16 |
| D/F, mole | 0.4176 | 0.4176 | 0.4176 | 0.4176 |
| Reflux ratio | 1.228 | 1.28 | 2.86 | 13.1 |
| Plate number | | | | |
| Condenser | 1 | 1 | 1 | 1 |
| Rectification Column | 2-7 | 2-7 | 2-6 | 2-7 |
| Upper catalytic bed | 8-12 | 8-9 | 7-8 | N/A |
| Lower catalytic bed | N/A | 10-17 | 10-17 | 8-15 |
| Stripping column | 13-18 | 18-23 | 18-23 | 16-21 |
| Reboiler | 19 | 24 | 24 | 22 |
| Low temperature catalyst, m³ | 11.6 | 4.66 | 4.66 | N/A |
| High temperature catalyst, m³ | N/A | 26.4 | 26.4 | 22.6 |
| Tower temperature, °C. | | | | |
| Rectification column | 48.3-100 | 48.3-101 | 48.6-122 | 48.3-154 |
| Upper catalytic bed | 120-170 | 120-131 | 125-128 | N/A |
| Lower catalytic bed | N/A | 136-171 | 136-160 | 164-174 |
| Stripping column | 177-186 | 178-186 | 168-186 | 172-186 |
| Pressure at tower top, bar | 11 | 11 | 11 | 11 |

*Conventional method, the low temperature dehydration catalyst did not work at high temperature.
**Conventional method, use high temperature dehydration catalyst.

When the methanol was fed from feed port 1, the liquid flow amount was more than the liquid flow amount in Example 1 because the methanol feeding contains water. Therefore, the tower diameter in this example was larger than the tower diameter in Example 1. The temperature distribution in the tower from theoretical calculation was similar to the tower temperature distribution shown in FIG. 5. The temperature of the lower catalytic bed in the dual-bed catalytic distillation system was lower than the temperature in the single-bed distillation system at the same position. Accordingly, the low temperature dehydration catalyst was better protected in dual-bed catalytic distillation system.

When the upper catalytic bed was moved a plate upper and methanol was fed from feed port 2, the reflux rate was raised to increase the conversion rate of methanol. The concentrations of DME at the tower top and water at the tower bottom respectively decreased to 99.3 wt % and 98.9 wt %.

When methanol was fed from feed port 3, only high temperature dehydration catalysts could be used in the single-bed distillation system because low temperature dehydration catalysts were damaged when the column temperature was higher than 160° C.

Example 3

Mixture of DME, Methanol and Water as the Feeding

The feeding came from the process for preparing methanol from syngas (with reference to U.S. Pat. No. 5,908,963). After separation, the concentration of carbon dioxide, DME, methanol and water in the product from the reactor were respectively 2.8 wt %, 49.7 wt %, 31.0 wt % and 16.5 wt %. The mixture could be fed at the top catalytic column or between the upper and lower catalytic beds. The reflux ratios were calculated to be 0.378 and 1.22. The results were shown in Table 5, Table 6 and FIG. 7.

TABLE 6

The results for the preparation of DME using single-bed and dual-bed catalytic distillation tower

| | Catalytic column | | |
|---|---|---|---|
| | Single-bed* | Dual-bed DME grade | Dual-bed |
| | Chemical | Chemical | Chemical |
| Feeding plate number | 7 | 7 | 9 |
| D/F, mole | 0.5278 | 0.5278 | 0.5278 |
| Reflux ratio | 0.354 | 0.378 | 1.22 |
| Plate number | | | |
| Condenser | 1 | 1 | 1 |
| Rectification Column | 2-7 | 2-7 | 2-6 |
| Upper catalytic bed | 8-12 | 8-9 | 7-8 |
| Lower catalytic bed | N/A | 10-14 | 10-14 |
| Stripping column | 13-18 | 15-20 | 15-20 |
| Reboiler | 19 | 21 | 21 |
| Low temperature catalyst, m$^3$ | 16.4 | 6.6 | 6.6 |
| High temperature catalyst, m$^3$ | N/A | 23.3 | 23.3 |
| Tower temperature, ° C. | | | |
| Rectification column | 48.3-64 | 48.3-66 | 48.3-96 |
| Upper catalytic bed | 89-173 | 94-125 | 101-104 |
| Lower catalytic bed | N/A | 140-172 | 134-167 |
| Stripping column | 179-186 | 179-186 | 174-186 |
| Pressure at tower top, bar | 11 | 11 | 11 |

*Conventional method, the low temperature dehydration catalyst did not work at high temperature.

Figure 7:
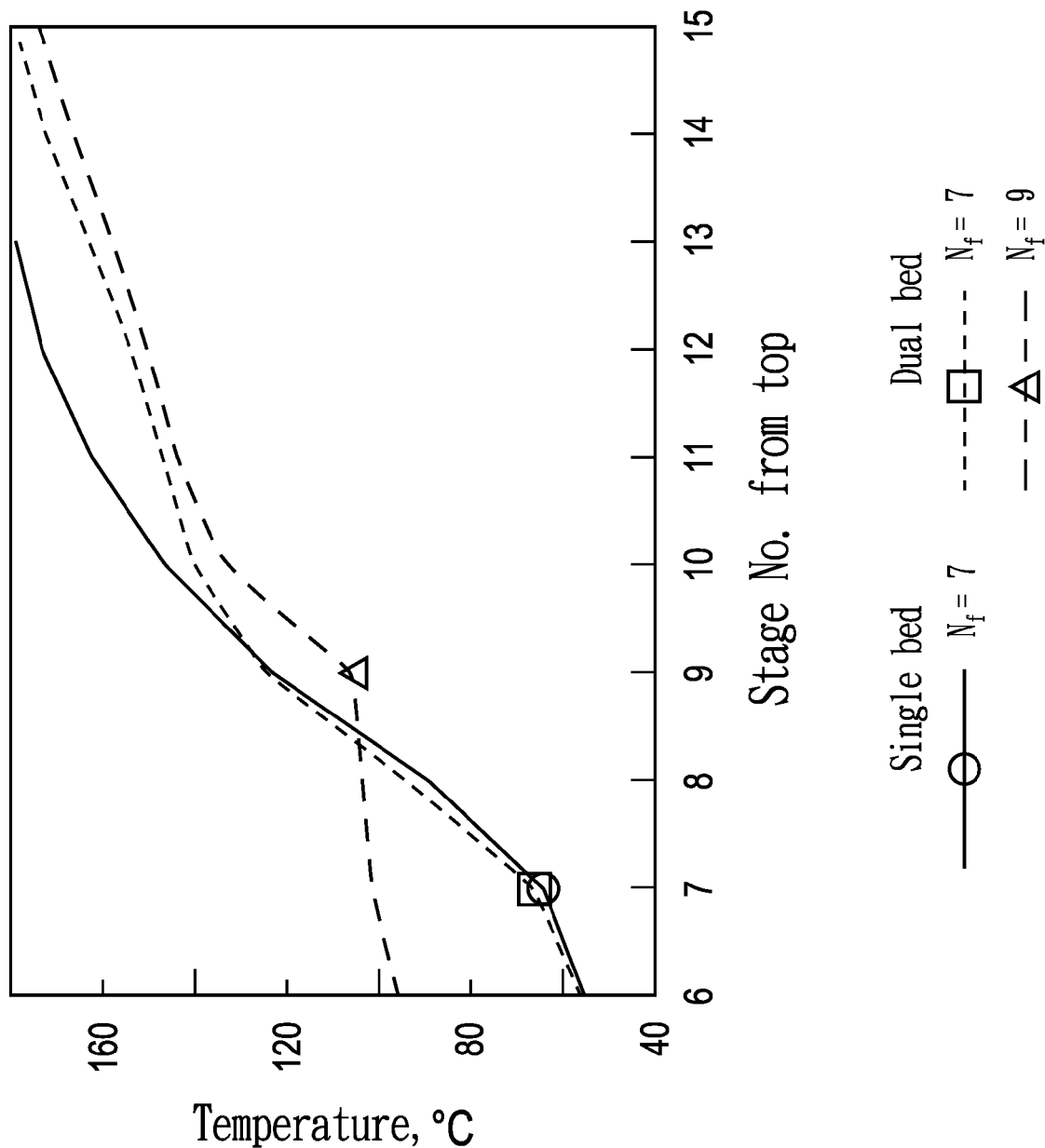
FIG. 7 is a diagram showing the tower temperature distribution in the catalytic distillation tower of the present invention with mixture feeding of DME, methanol and water.

FIG. 7 showed the temperature changes in the catalytic column. Feeding the mixture at the feed port 2 between the upper and lower catalytic beds alleviated rapid temperature changes in the catalytic column and simultaneously protected the catalysts in the low temperature catalytic bed from being damaged. As shown in FIG. 3, heat exchange/reflux might be

TABLE 5

Stream composition during the catalytic distillation process

| | Catalytic Column | | | | | | | | |
|---|---|---|---|---|---|---|---|---|---|
| DME grade | Single-bed* Chemical | | | Dual-bed Chemical | | | Dual-bed Chemical | | |
| Feeding plate number**** | 7 | | | 7 | | | 9 | | |
| Stream*** | 1 | 5 | 6 | 1 | 5 | 6 | 2 | 5 | 6 |
| Water, kg/hr | 3190 | 0 | 4870 | 3190 | 0 | 4870 | 3190 | 0 | 4864 |
| Methanol, kg/hr | 5994 | 13.6 | 4.9 | 5994 | 13.7 | 4.9 | 5994 | 25 | 15 |
| DME, kg/hr | 9610 | 13905 | 0 | 9610 | 13905 | 0 | 9610 | 13890 | 0 |
| Total, kg/hr | 18794 | 13919 | 4875 | 18794 | 13919 | 4875 | 18794 | 13915 | 4879 |

*Conventional method, the low temperature dehydration catalyst did not work at high temperature.

***Stream composition at the feed ports 1 and 2, condenser output 5 and reboiler output 6 shown in FIG. 3.

****Feeding at plate number 7 means feeding from feed port 1, feeding at plate number 9 means feeding from feed port 2.

carried out at the flash zone 9 to control the temperature at the catalytic column and protect the low temperature dehydration catalyst from being damaged.

Example 4

Mixture of DME Methanol Carbon Dioxide and Water as the Feeding

The feeding came from the process for preparing methanol from syngas (with reference to U.S. Pat. No. 5,908,963). After separation, the concentration of carbon dioxide, DME, methanol and water in the product from the reactor were respectively 2.8 wt %, 49.7 wt %, 31.0 wt % and 16.5 wt %. The carbon dioxide could not be liquefied because of the limitation of the tower pressure. Thus, an overhead condenser was equipped on the top of the catalytic distillation tower. The results were shown in Table 7. The obtained DME contains 1.36 wt % of carbon dioxide, so it flowed back to the catalytic distillation tower for purification. The carbon dioxide and DME in gas phase were respectively 25 wt % and 75 wt %. They also needed to be re-purified in the catalytic distillation tower.

TABLE 7

The results for the preparation using dual-bed catalytic distillation tower

|  | Catalytic column Dual-bed | | | |
| --- | --- | --- | --- | --- |
| Feeding plate number**** | 7 | | | |
| Stream*** | 1 | 4 | 5 | 6 |
| Water | 3101 | 0 | 0.6 | 4733 |
| Methanol | 5826 | 0.1 | 12.7 | 4.7 |
| Dimethyl ether | 9341 | 1038 | 12479 | 0 |
| Carbon dioxide | 526 | 354 | 172 | 0 |
| Total, kg/hr | 18794 | 1392 | 12664 | 4738 |
| Results | | | | |
| D/F, mole | 0.538 | | | |
| Gas/tower top distillate ratio | 0.1 | | | |
| Reflux ratio | 0.343 | | | |
| Plate number | | | | |
| Condenser | 1 | | | |
| Rectification Column | 2-7 | | | |
| Upper catalytic bed | 8-9 | | | |
| Lower catalytic bed | 10-13 | | | |
| Stripping column | 14-19 | | | |
| Reboiler | 20 | | | |
| Low temperature catalyst, m³ | 6.9 | | | |
| High temperature catalyst, m³ | 19.4 | | | |
| Tower temperature, ° C. | | | | |
| Rectification column | 41-68 | | | |
| Upper catalytic bed | 80-112 | | | |
| Lower catalytic bed | 143-185 | | | |

TABLE 7-continued

The results for the preparation using dual-bed catalytic distillation tower

|  | Catalytic column Dual-bed |
| --- | --- |
| Stripping column | 190-193 |
| Pressure at tower top, bar | 13 |

***Stream composition at the feed ports 1 and 2, condenser output 5 and reboiler output 6 shown in FIG. 3.
****Feeding at plate number 7 means feeding from feed port 1.

Testing Example

Catalyst Aging Test

In the testing example, a catalyst aging test was conducted on a low or high temperature dehydration catalyst with a feeding containing 50 wt % methanol and 50 wt % water in a continuous downflow fixed-bed reactor. The feeding was fed at a rate of 42 g/h at 120° C. and 160 psi. The continuous downflow fixed-bed reactor was 92.4 centimeters long with an inner diameter of 2.07 centimeters. The continuous downflow fixed-bed reactor was filled with 96 ml of a dehydration catalyst by a gradient packing method to provide the catalytic bed a nearly uniform temperature and to minimize the wall and bypassing effects. The upstream of the continuous downflow fixed-bed reactor was a preheat zone filled with $SiO_2$. Mass balance between feeding and outlet product was 99%.

Each sample was analyzed with a gas chromatograph (Agilent Technologies Model 6890 N, TCD model) coupled with the ChemStation software. Since the boiling point of dimethyl ether (DME) was much lower than those of methanol and water, it was difficult to obtain an accurate DME analysis by gas chromatograph. Accordingly, only methanol and water were taken into consideration to calculate mass fraction of methanol. The methanol conversion ($X_{MeOH}$) was calculated by the following equation (1):

$$X_{MeOH} = \frac{\xi_{MeOH}}{F_{MeOH}} \times 100\% \quad (1)$$

Said $\xi_{MeOH}$ was further calculated by the following equation (2):

$$wt_{MeOH}|_{product} = \frac{(F_{MeOH} - \xi_{MeOH}) \times 32}{(F_{MeOH} - \xi_{MeOH}) \times 32 + \left(F_{H2O} + \frac{\xi_{MeOH}}{2}\right) \times 18} \quad (2)$$

In equation (1), $\xi_{MeOH}$ and $F_{MeOH}$ respectively represented outlet and inlet methanol mass flow rates. In equation (2), $wt_{MeOH}$ represented outlet methanol mass concentration, $F_{H2O}$ represented inlet water mass flow rate, and $\xi_{MeOH}$ represented outlet methanol mass flow rate.

(a) Amberlyst® 35

Herein, a catalyst aging test was conducted on Amberlyst® 35 at 120° C. As shown in Table 8, the average methanol conversion catalyzed by Amberlyst® 35 varied with different feeding in the test run. The period on stream totaled 180 days and the period of catalyst aging test was 120 days. The initial average conversion for 99.5 wt % methanol was about 35.8%. After aging at 120° C. with 50 wt % methanol solution for 50 days, the average conversion for 99.5 wt % methanol decreased to 32.3%. The average conversion for 99.5 wt % methanol solution further decreased to 21% at the end of 120 aging days. The result demonstrated that the activity of Amberlyst® 35 is sufficient to catalyze methanol dehydration even under severe conditions of 120° C. and 50 wt % of methanol solution and that Amberlyst® 35 still remains active for more than 120 days.

TABLE 8 the catalyst aging test of Amberlyst ® 35

| Test run | activity | aging | aging | activity | aging | aging | activity |
|---|---|---|---|---|---|---|---|
| Stream (days) | 21-30 | 39-49 | 77-88 | 92-97 | 109-119 | 158-167 | 170-180 |
| Catalyst aging (days) | 0 | 11 | 50 | 50 | 72 | 120 | 120 |
| Feeding, MeOH (wt %) | 99.5 | 50.0 | 50.0 | 99.5 | 50.0 | 50.0 | 99.5 |
| Average conversion (%) | 35.8 | 7.32 | 5.61 | 32.3 | 4.65 | 3.61 | 20.3 |

(b) Amberlyst® 70

Herein, catalyst aging tests were conducted on Amberlyst® 70 at 120° C. and 150° C., respectively.

As shown in Table 9, the average methanol conversion catalyzed by Amberlyst® 70 varied with different feeding in the test run. The period on stream totaled 100 days and the period of catalyst aging test was 58 days. The initial average conversion for 99.5 wt % methanol was about 14.9%. After aging at 120° C. with 50 wt % methanol solution for 58 days, the average conversion for 99.5 wt % methanol exhibited a slight decrease to 12.9%. The result demonstrated that the activity of Amberlyst® 70 does not deactivate at 120° C. or by 50 wt % of methanol solution.

TABLE 9 the catalyst aging test of Amberlyst ® 70 at 120° C.

| Test run | activity | Aging | activity |
|---|---|---|---|
| Stream (days) | 1-18 | 19-76 | 77-100 |
| Catalyst aging (days) | 0 | 58 | 0 |
| Feeding, MeOH (wt %) | 99.5 | 50.0 | 99.5 |
| Average conversion (%) | 14.9 | 1.43 | 12.9 |

As shown in Table 10, the average methanol conversion catalyzed by Amberlyst® 70 varied with different feedings in the test run. The period on stream totaled 24 days and the periods of catalyst aging tests were 10 and 17 days. The conversion at $3^{th}$ stream day for 99.5 wt % methanol was about 42.9%. After aging at 150° C. with 50 wt % methanol solution for 10 days and 17 days, the respective conversions for 50 wt % methanol were 20.1% and 14.1%. The results demonstrated that Amberlyst® 70 is useful to catalyze methanol dehydration at 150° C. and with 50 wt % of methanol solution for 24 days or more.

TABLE 10 the catalyst aging test of Amberlyst ® 70 at 150° C.

| Test run | activity | aging | aging |
|---|---|---|---|
| Stream (day) | $3^{th}$ | $17^{th}$ | $24^{th}$ |
| Catalyst aging (days) | 0 | 10 | 17 |
| Feeding, MeOH (wt %) | 99.5 | 50 | 50.0 |
| conversion (%) | 42.9 | 20.1 | 14.1 |

Example 5

Crude Methanol as the Feeding

According to Tables 8 and 10, the reaction rate of methanol dehydration catalyzed with Amberlyst® 70 was assumed to be 35% of that with Amberlyst® 35, and the Amberlyst® 70 is useful to catalyze methanol dehydration at 150° C.

In the instant Example, the upper catalytic bed was filled with a low temperature dehydration catalyst, Amberlyst® 35, and the lower catalytic bed was filled with a high temperature dehydration catalyst, Amberlyst® 70.

Three different crude methanols were respectively fed to the dual-bed catalytic distillation tower of the present invention directly for dehydration without further purification. Considering the properties of Amberlyst® 35 and Amberlyst® 70, the feeding plate number of the catalytic column, the reflux ratio and D/F in the dual-bed catalytic distillation tower were rebuilt and simulated to produce 99.9% DME. Furthermore, the tower pressure was adjusted down to 9 bar from 11 bar, thus the temperature of the upper and the lower catalytic beds also lowered to the range from 110° C. to 125° C. and the range from 125° C. to 150° C., respectively.

TABLE 11

The results for the preparation of DME using dual-bed catalytic distillation tower with Amberlyst ® 35 and Amberlyst ® 70

| | Catalytic column | | |
|---|---|---|---|
| | Dual-bed | Dual-bed Feeding | Dual-bed |
| | 99.9 wt % MeOH 0.1 wt % $H_2O$ | 90 wt % MeOH 10 wt % $H_2O$ | 31 wt % MeOH 16.5 wt % $H_2O$ 49.7 wt % DME |
| Feeding plate number | 7 | 9 | 9 |
| D/F, mole | 0.4993 | 0.4176 | 0.5277 |
| Reflux ratio | 2.59 | 4.88 | 3.46 |
| Plate number | | | |
| Condenser | 1 | 1 | 1 |
| Rectification Column | 2-7 | 2-6 | 2-6 |
| Upper catalytic bed filled with Amberlyst ® 35 | 8-12 | 7-8 | 7-8 |
| Lower catalytic bed filled with Amberlyst ® 70 | 13-25 | 11-18 | 10-14 |
| Stripping column | 26-38 | 19-25 | 15-20 |
| Reboiler | 39 | 26 | 21 |
| Amount of Amberlyst ® 35 in upper catalytic bed, kg | 583 | 766 | 766 |
| Amount of Amberlyst ® 70 in lower catalytic bed, kg | 583 | 766 | 766 |
| Tower temperature, ° C. | | | |
| Rectification column | 40.3-111.1 | 40.3-118.7 | 40.3-113.5 |
| Upper catalytic bed | 112.0-121.4 | 123.1-125.8 | 117.9-120.3 |

TABLE 11-continued

The results for the preparation of DME using dual-bed catalytic distillation tower with Amberlyst ® 35 and Amberlyst ® 70

| | Catalytic column | | |
|---|---|---|---|
| | Dual-bed | Dual-bed Feeding | Dual-bed |
| | 99.9 wt % MeOH 0.1 wt % H₂O | 90 wt % MeOH 10 wt % H₂O | 31 wt % MeOH 16.5 wt % H₂O 49.7 wt % DME |
| Lower catalytic bed | 123.9-149.1 | 131.9-146.9 | 135.4-149.5 |
| Stripping column | 151.2-179.7 | 151.7-178.2 | 155.6-177.7 |
| Pressure at tower top, bar | 9 | 9 | 9 |

As shown in Table 11, both crude methanol and the mixture of DME, methanol and water were applicable as feedings, and were respectively fed into the dual-bed catalytic distillation tower directly for dehydration to produce DME. By lowering the temperature range, Amberlyst® 70 kept its catalytic activity and ensured a longer catalytic life. Accordingly, a dual-bed catalytic distillation tower filled with non-halogenated and halogenated divinyl-benzene cross-linked sulfonated polystyrene resin is more useful for the production of DME in industry application.

What stated above is only preferred embodiments of the present invention, which is illustrative only and not restrictive. Changes, modifications, or the equivalents may be made by those skilled in the art without departing from the spirits and scope of the present invention as defined by the claims, but will fall within the scope of protection of the present invention.

What is claimed is:

1. A dual-bed catalytic distillation tower comprising a catalytic column having an upper catalytic bed and a lower catalytic bed, at least one feed port set at a top of the upper catalytic bed, between the upper and lower catalytic beds, and at a bottom of the lower catalytic bed; wherein the upper catalytic bed is filled with low temperature dehydration catalysts and the lower catalytic bed is filled with high temperature dehydration catalysts, wherein a temperature of the upper catalytic bed ranges from 85° C. to 125° C., and a temperature of the lower catalytic bed ranges from 125° C. to 180° C.

2. The dual-bed catalytic distillation tower according to claim 1, wherein the low temperature dehydration catalyst is a non-halogenated divinyl-benzene cross-linked sulfonated polystyrene resin having an acid capacity more than 4 meq/g.

3. The dual-bed catalytic distillation tower according to claim 2, wherein the non-halogenated divinyl-benzene cross-linked sulfonated polystyrene resin comprises Amberlyst® 15 acid ion exchange resin, Amberlyst® 35 acid ion exchange resin, Purolite® CT-275, Purolite® CT-276 or any combination thereof.

4. The dual-bed catalytic distillation tower according to claim 1, wherein the high temperature dehydration catalyst is a halogenated divinyl-benzene cross-linked sulfonated polystyrene resin having an acid capacity more than 2 meq/g.

5. The dual-bed catalytic distillation tower according to claim 4, wherein the halogenated divinyl-benzene cross-linked sulfonated polystyrene resin comprises Amberlyst® 70 acid ion exchange resin, Purolite® CT-482 or their combination.

6. A method for preparing dimethyl ether (DME) by using the dual-bed catalytic distillation tower according to claim 1, wherein a feeding containing methanol is fed to the catalytic distillation tower at the top of the upper catalytic bed, between the upper and lower catalytic beds, or at the bottom of the lower catalytic bed at a tower pressure ranging from 7 to 12 bar for dehydration to obtain DME.

7. The method for preparing DME according to claim 6, wherein at least one flash zone at the top of the upper catalytic bed, between the upper catalytic bed and the lower catalytic bed, and at the bottom of the lower catalytic bed is reserved for heat exchange and reflux.

8. The method for preparing DME according to claim 6, wherein the feeding is anhydrous methanol and is fed at the top of the upper catalytic bed.

9. The method for preparing DME according to claim 6, wherein the feeding is a mixture of DME, methanol and water obtained from syngas and is fed between the upper and lower catalytic beds.

10. The method for preparing DME according to claim 6, wherein the feeding is crude methanol and is fed at the bottom of the lower catalytic bed or between the upper and lower catalytic beds.

11. The method for preparing DME according to claim 6, wherein the low temperature dehydration catalyst is a non-halogenated divinyl-benzene cross-linked sulfonated polystyrene resin having an acid capacity more than 4 meq/g.

12. The method for preparing DME according to claim 11, wherein the non-halogenated divinyl-benzene cross-linked sulfonated polystyrene resin comprises Amberlyst® 15 acid ion exchange resin, Amberlyst® 35 acid ion exchange resin, Purolite® CT-275, Purolite® CT-276 or any combination thereof.

13. The method for preparing DME according to claim 6, wherein the high temperature dehydration catalyst is a halogenated divinyl-benzene cross-linked sulfonated polystyrene resin having an acid capacity more than 2 meq/g.

14. The method for preparing DME according to claim 13, wherein the halogenated divinyl-benzene cross-linked sulfonated polystyrene resin comprises Amberlyst® 70 acid ion exchange resin, Purolite® CT-482 or their combination.

* * * * *